United States Patent [19]
Ravo et al.

[11] Patent Number: 4,716,900
[45] Date of Patent: Jan. 5, 1988

[54] INTRAINTESTINAL BYPASS GRAFT

[75] Inventors: Biagio Ravo, Garden City, N.Y.; Thomas E. Sloane, Jr., West Redding, Conn.; Christine L. Regan, Port Washington, N.Y.

[73] Assignee: Pfizer Hospital Products Group, Inc., New York, N.Y.

[21] Appl. No.: 861,692

[22] Filed: May 9, 1986

[51] Int. Cl.⁴ ............................................. A61B 17/12
[52] U.S. Cl. .................................. 128/334 R; 623/12
[58] Field of Search ............... 623/11, 12, 1; 604/282, 604/280; 128/DIG. 21, 334 R, 334 C, 303 R

[56] References Cited

U.S. PATENT DOCUMENTS

| | | | |
|---|---|---|---|
| 1,470,707 | 10/1923 | Bates | 128/334 R |
| 4,134,405 | 1/1979 | Smit | 128/303 R |
| 4,315,509 | 2/1982 | Smit | 128/303 R |

FOREIGN PATENT DOCUMENTS 885054  12/1961  United Kingdom ............... 604/280

Primary Examiner—Michael H. Thaler
Attorney, Agent, or Firm—Peter C. Richardson; Lawrence C. Akers; John L. LaPierre

[57] ABSTRACT

An improved intraintestinal bypass graft for attachment in the lumen of a resectioned intestine or duct upstream of the anastomosis site in order to protect the healing anastomosis comprises an elongated tube formed of a thin, highly flexible, water-impervious wall material terminating at its distal end in a short, reduced diameter nipple. The surgical procedure for implanting the bypass graft can be simplified and shortened in time by readily fitting the distal nipple over one end of an elongated pliable leader, or alternatively over the terminal anvil nut of a circular anastomosis surgical stapler, and then drawing the leader or stapler body through the patient's anus to pull the distal end of the bypass graft out of the anus. The need to tie the distal end of the bypass graft to the leader or surgical stapler is eliminated.

7 Claims, 3 Drawing Figures

INTRAINTESTINAL BYPASS GRAFT

BACKGROUND OF THE INVENTION

The present invention is directed to an intraintestinal bypass graft of the type disclosed in the copending U.S. patent application Ser. No. 538,347, filed Oct. 3, 1983, now abandoned, by Dr. Biagio Ravo, the content of which application is incorporated by reference herein in its entirety, and in the following articles:

Biagio Ravo and Ralph Ger, "Management of Esophageal Dehiscences by an Intraluminal Bypass Tube", *Amer. Jour. Surg.*, Vol. 149, pp. 733 to 738 (June 1985);

G. Castrini, R. Ger, G. Pappalardo, B. Ravo, P. Trentino and M. Pisapia, "Intracolonic By-pass: A New Technique to Prevent Anastomotic Complications in Colon and Rectal Surgery", *Ital. Jour. Surg. Sci.*, Vol. 14, No. 3, pp. 189 to 193 (1984); and Biagio Ravo and Ralph Ger, "Temporary Colostomy—An Outmoded Procedure? A Report on the Intracolonic Bypass", *Dis. Col. & Rect.*, Vol. 28, No. 12, pp. 904 to 907 (December 1985).

The surgical techniques for implanting the bypass graft of this type are described in detail in the above patent application and articles. Briefly, the proximal end of the thin-walled, highly flexible, water-impervious, cylindrical bypass graft is first sutured to the inner wall of the proximal segment of the sectioned intestine or duct. The posterior wall of the intestine or duct anastomosis is then sutured, after which the distal end of the graft is tied with a suture to an end of a pliable elongated leader (e.g. a rectal tube) and the leader passed through the distal colon segment and then drawn through the patient's anus. When the leader has been fully drawn through the anus an end of the bypass graft is exposed, which allows the graft to be cut to its proper length. Finally, the anterior wall of the intestine or duct anastomosis is sutured. The procedure is the same when the intestine or duct is resectioned with a circular anastomosis surgical stapler (see e.g. U.S. Pat. No. 4,351,466) instead of sutured, except that after the graft is sutured to the inner wall of the intestine, the stapler body is inserted through the anus and advanced to the anastomosis site, the distal end of the graft is tied around the terminal anvil nut of the stapler, the stapler is activated to form the anastomosis all at once, and the stapler body is then withdrawn through the anus, pulling the distal end of the graft along with it (see the aforementioned December 1985 article in *Dis. Col. & Rect.*).

The graft and procedure described above may be successfully used to protect the anastomosis site in a resectioned intestine or duct and eliminate the need for temporary colostomies. However, the need for the surgeon to securely tie the distal end of the cylindrical graft around the end of the pliable leader, of the stapler anvil nut, can significantly and undersirably extend the total time of the surgical procedure. It is an object of the present invention to alleviate this problem associated with the surgical Procedure described above.

SUMMARY OF THE INVENTION

The present invention comprises a bypass graft of the type suitable for attachment in the lumen of a resectioned intestine or duct upstream of the anastomosis thereof in order to protect the anastomosis site, said bypass graft comprising (a) an elongated tube having proximal and distal ends and formed of a thin water-impervious wall material having sufficient flexibility to conform to the natural movements of the intestine or duct surrounding it, and (b) reinforcing means extending around the proximal end of the tube for rendering that end stronger than said thin wall material but still sufficiently flexible to conform to the natural movements of the intestine or duct. According to the present invention, the elongated tube terminates at its distal end in a relatively short nipple of substantially reduced cross-section (as compared to the remainder of the tube). Preferably, the great majority of the length of the elongated tube is substantially cylindrical with a substantially constant diameter, the relatively short nipple is also elongated and substantially cylindrical with a substantially constant diameter, and the longitudinal axis of the nipple coincides with an extension in the distal direction of the longitudinal axis of said substantially cylindrical major portion of the elongated tube.

By using the improved bypass graft of the present invention the need for the surgeon to take the time to tie the distal end of the graft to the leader or circular anastomosis stapler is eliminated. The thin, highly flexible wall material of the distal nipple can be easily rolled backward upon itself and then readily rolled forward again over the end of an elongated leader or over a surgical stapler anvil nut to bring about a tight and secure frictional fit between the graft and leader or stapler.

If desired, the surgeon may be provided with a pre-assembled combination of bypass graft and pliable elongated leader, with one end of the leader being securely received in a tight frictional fit within the nipple. The present invention further includes such a pre-assembled combination of bypass graft and leader. The leader can be, for example, a conventional rectal tube, an elongated non-hollow bar of pliable material, or any other similar article.

DETAILED DESCRIPTION OF THE INVENTION

The invention will be described in detail with reference to a preferred embodiment thereof. Reference to this embodiment does not limit the scope of the invention, which is limited only by the scope of the claims. In the drawings:

Figure 1:
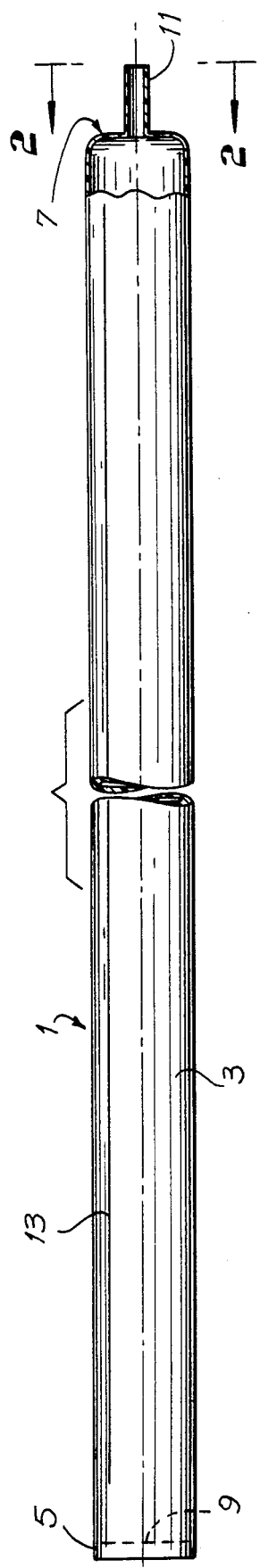
FIG. 1 is a side elevational view of a bypass graft of the present invention, with a distal portion of the graft shown in section.
Figure 2:
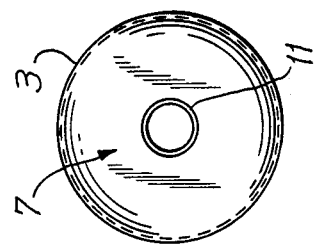
FIG. 2 is an end elevational view of the bypass graft of FIG. 1.
Figure 3:
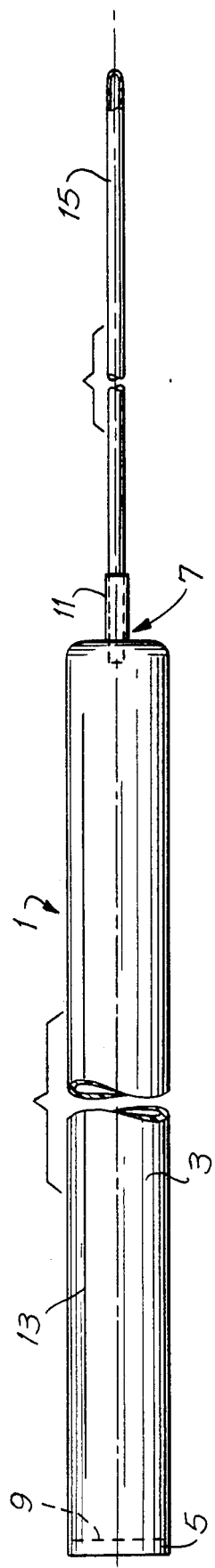
FIG. 3 is a side elevational view of the bypass graft of FIG. 1 in a pre-assembled combination with a leader, with a distal portion of the leader shown in section.

An intraintestinal bypass graft 1 of the invention is shown in FIGS. 1 and 2. Bypass graft 1 comprises an elongated tube 3 having a proximal end 5 and a distal end 7, and a reinforcing means extending around the proximal end 5 of tube 3. The wall of elongated tube 3 is formed of a thin water-impervious material having sufficient flexibility to conform to the natural movements of an intestine or duct surrounding it, for example a silicone elastomer or latex polymer having a thickness of from about 0.05 mm. to about 1 mm. Reinforcing means 9 may extend around the outer surface or the inner surface (as shown in FIGS. 1 and 3), or both, of the proximal end 5 of tube 3. The reinforcing means may include material distinct from that of tube 3, or alternatively, may be formed by lap folding one or more proximal marginal portions of the tube upon themselves. The purpose of the reinforcing means is to strengthen the proximal end 5 of tube 3, so that it can be readily sutured to the inner wall of an intestine or duct without tearing, while still permitting that proximal end 5 to retain sufficient flexibility to conform to the natural movements of the intestine or duct surrounding it. In the embodiment shown in the figures, the reinforcing means 9 is a woven fabric band or collar (e.g. polyester) adhesively bonded to the inner surface of the proximal end 5 of the tube 3.

Except for the configuration of the distal end region of tube 3, bypass graft 1 is substantially identical to the bypass graft disclosed in said pending U.S. application Ser. No. 538,347. As is shown in the figures herein, the elongated tube 3 is substantially cylindrical with a substantially constant diameter (typically from about 1 to about 2 inches) over a great majority of its length, but terminates at its distal end 7 in a relatively short nipple 11 of substantially reduced cross-section (as compared to the major portion of tube 3). Most preferably, nipple 11 has an elongated substantially cylindrical shape with a substantially constant diameter, and the longitudinal axis of nipple 11 coincides with an extension of the longitudinal axis of the substantially cylindrical major portion of tube 3.

All of tube 3 (including nipple 11) is preferably a single one-piece unitary article having a substantially constant wall thickness throughout. Most preferably, tube 3 is made by dipping an appropriately-configured mandrel including a terminal portion complementary to the desired shape of the nipple 11 into, e.g., a bath of a silicone elastomer or latex material. After curing of the wall material of the tube 3, a longitudinally-extending stripe 13 of radiopaque material may be applied onto the tube to provide for X-ray observation of the bypass graft 1 after its implantation.

The distal nipple 11 is dimensioned so that it can be readily and quickly fitted by the surgeon during an operation in a tight frictional fit over the end of a suitable leader, such as a rectal tube, or over the terminal anvil nut of a conventional circular anastomosis surgical stapler. The inherent flexibility of the thin-walled material of the tube 3 gives the nipple 11 the capability to expand outwardly to receive a leader end or anvil nut, and then to securely hold the tube 3 to the leader or stapler with the nipple 11 in a tensioned state gripping the leader end or anvil nut. An unwanted separation of the graft 1 and leader or stapler as the graft is being drawn towards or through the patient's anus is thus very unlikely. Preferably, the diameter of the nipple 11 is from about 0.25 in. to about 0.35 in. The preferred ratio of the nipple diameter to the diameter of the substantially cylindrical major portion of tube 3 is from about 0.15 to about 0.25. Typically, the length of bypass graft 1 is about 30 in. and the length of nipple 11 is about 1 in.

FIG. 3 shows a pre-assembled combination of a bypass graft 1 of the invention and a pliable elongated leader 15. The leader is hollow along its length, open at its proximal end (within nipple 11) but closed at its distal end to prevent accumulation of bodily materials as it is passed through the colon. The convenience to the surgeon intending to resection the patient's intestine or duct by suturing can be still further enhanced by providing the bypass graft 1 pre-assembled with a leader 15, as is shown in FIG. 3. Typically, leader 15 is about 18 in. long. The hollow structure of leader 15 permits control of its stiffness (by adjusting its wall thickness) while maintaining a fixed outside diameter.

We claim:

1. A bypass graft suitable for attachment in the lumen of a resectioned intestine or duct upstream of the anastomosis thereof comprising
   an elongated tube having proximal and distal ends and formed of a thin water-impervious wall material having sufficient flexibility to conform to the natural movements of the intestine or duct surrounding it, and
   reinforcing means extending around the proximal end of said tube for rendering said end stronger than said thin wall material but still sufficiently flexible to conform to said natural movements,
   with said elongated tube abruptly terminating at its distal end in a relatively short nipple of substantially reduced cross-section.

2. A bypass graft of claim 1 wherein said elongated tube includes a substantially cylindrical portion with a substantially constant diameter proximal of said distal end nipple, said substantially cylindrical portion extending over a great majority of the length of said tube.

3. A bypass graft of claim 2 wherein said nipple is elongated and has a longitudinal axis coincident with a distal extension of the longitudinal axis of said substantially cylindrical major portion of the elongated tube.

4. A bypass graft of claim 3 wherein said nipple has a substantially cylindrical shape with a substantially constant diameter.

5. A bypass graft of claim 4 wherein the diameter of said nipple is from about 0.15 to about 0.25 times the diameter of said substantially cylindrical major portion of the elongated tube.

6. A bypass graft of claim 4 wherein the diameter of said nipple is from about 0.25 in. to about 0.35 in.

7. In combination
   a bypass graft of claim 1 and
   an elongated pliable leader capable of being drawn through the anus of a patient,
   with one end of said leader being securely received in a tight frictional fit within said nipple independently coupling said bypass graft and said leader.

* * * * *